(12) United States Patent
Lang et al.

(10) Patent No.: US 6,855,520 B2
(45) Date of Patent: Feb. 15, 2005

(54) CELL VOLUME-REGULATED HUMAN KINASE H-SGK

(76) Inventors: Florian Lang, Im Rotbad 52, Tubingen (DE), 72076; Siegfried Waldegger, Kingersheimer Str. 36, Tubingen (DE), 72071

(*) Notice: Subject to any disclaimer, the term of this patent is extended or adjusted under 35 U.S.C. 154(b) by 318 days.

(21) Appl. No.: 10/000,039

(22) Filed: Dec. 4, 2001

(65) Prior Publication Data

US 2003/0003559 A1 Jan. 2, 2003

Related U.S. Application Data

(62) Division of application No. 09/031,295, filed on Feb. 26, 1998, now Pat. No. 6,326,181.

(30) Foreign Application Priority Data

Feb. 28, 1997 (DE) .......................................... 197 08 173

(51) Int. Cl.[7] .......................... C12P 19/30; C12P 19/34; C12N 9/12; C07H 21/02; C07H 21/04

(52) U.S. Cl. ........................ 435/89; 435/194; 435/91.3; 435/91.1; 435/91.21; 536/23.2; 536/23.1

(58) Field of Search ........................ 435/194, 89, 91.1, 435/91.21, 91.3, 320.1, 252.3, 6; 536/23.2, 23.1

(56) References Cited

U.S. PATENT DOCUMENTS

5,863,780 A  1/1999  Au-Young et al. .......... 435/194

FOREIGN PATENT DOCUMENTS

| EP | 0 416 499 | 3/1991 |
| EP | 0 887 081 | 12/1998 |
| WO | 98/11234 | 3/1998 |

OTHER PUBLICATIONS

Adams et al., Nature, 377 ( 6547 Suppl), 3–174, 1995.*
Waldegger et al.,"cloning and characterization of a putative human serine/threonine protein kinase transcriptionally modified during anisotonic alterations of cell volume" Proceedings of the National Academy of Sciences of USA, 94(9):4440–4445 (Apr. 1997) ©Cell Biology.
EMBL Database, Heidelberg, FRG Accession No. EMHUM2: Y10032 Feb. 6, 1997, Waldegger, S. "*H sapiens* mRNA for putative serine/threonine protein kinase" XP002112098.
Webster et al., "Characterization of *sgk*, a Novel Member if the Serine/Threonine Protein Kinase Gene Family Which is Transcriptionally Induced by Glucocorticoids and Serum" *Mol. Cell Biol.* 13:2031–2040 (1993).
Burg, "Molecular basis of osmotic regulation" *Am. J/Physiol* 268:F983–F996 (1995) ©the American Physiological Society.
Häussinger et al., "Regulation of cell function by the cellular hydration state" *Am. J. Physi l* 267:E343–E355 (1994) ©the American Physiological Society.
Minton, "The effect of volume occupancy upon the thermodynamic activity of proteins: some biochemical consequences" *Moll. Cell. Biochem*, 55:119–140 (1983) ©Martinus Nijhoff Publishers.
McManus et al., "Regualtion of Cell Volume in Health and Disease" *New England J. Med* 333 (19):1260–1266 (1995).
Demerdash et al., "Pathways through which glucose induces a rise in [$Ca^{2+}$]i of polymorphonuclear leukocytes of rats" *Kidney International* 50:2032–2040 (1996) ©International Society of Nephrology.
Häussinger et al., "Cellular hydration state: an important dterminant of protein catabolism in heath disease" *Lancet* 341:1330–1332 (1993).
Burg, "Molecular Basis for Osmoregulation fo Organic Osmolytes in Renal Medullar Cells" *J. Exp. Zool.* 268:171–175 (1994) ©Wiley–Liss, Inc.
Norenberg, "Astrocyte Responses to CNC Injury" *J. of Neuropathology and Exp. Neuro.* 53(3):213–220 (1994) ©American Association of Neuropathologists.
Kreis et al., "Localized $^1$H NMR Spectroscopy in Patients with chronic Hepatic Encephalopathy. Analysis of Changes in Cerebral Glutamine, Choline and Inositols" *NMR Biomed*. 4:109–116 (1991) ©John Wiley & Sons, Ltd.
McClelland et al., "Interactions among regulators of RNA abundance characterized using RNA fingerprinting by arbitrarily primed PCR" *Nucleic Acids. Res* 22(21):4419–4431 (1994) ©Oxford University Press.
Sanguineti et al., "Rapid Silver Staining and Recovery of PCR Products Separated on Polyacrylamide Gels" Short Technical Reports *Biotechniques* 17(5):915–919 (1994).
Pearson et al., "Improved tools for biological sequence comparison" *Proc. Natl. Acad. Sci. USA* 85:2444–2448 (1988).
Imaizumi et al., "Differential expression of *sgk* mRNA, a member of the Ser/Thr protein kinase gene family, in rat brain after CNS injury" *Mol. Brain Res*. 26:189–196 (1994) ©Elsevier Science B.V.
Richards et al., "Overlan Cell Differentiation: A Cascade of Multiple Hormones, Cellular Signals, and Regulated Genes" *Recent Prog. Horm. Res*. 50:223–254 (1995).

(List continued on next page.)

*Primary Examiner*—Maryam Monshipouri
(74) *Attorney, Agent, or Firm*—Foley & Lardner LLP

(57) ABSTRACT

The present invention relates to the cloning and characterization of a human serine/threonine kinase (h-sgk: serum and glucocorticoid dependent kinase). The invention furthermore relates to reagents for diagnosing conditions associated with a change in cell volume and/or in "macromolecular crowding" in the body, such as, for example, hypernatremia, hyponatremia, diabetes mellitus, renal failure, hypercatabolism, hepatic encephalopathy, inflammation and microbial or viral infections. The present invention additionally relates to pharmaceuticals comprising the h-sgk, nucleic acids which code for the h-sgk, or receptors, in particular antibodies, which specifically bind to the h-sgk.

15 Claims, 8 Drawing Sheets

OTHER PUBLICATIONS

Webster et al., "Immediate–early Transcriptional Regulation and Rapid mRNA Turnover of a Putative Serine/Threonine Protein Kinase" *J– Biol. Chem.* 268(16):11482–11485 (1993) ©The American Society for Biochemistry and Molecular Biology, Inc.

Sigma Catalog, 1994.

* cited by examiner

FIG. IA

```
CACGAGGGAG CGCTAACGTC TTTCTGTCTC CCCGCGGTGG TG ATG ACG GTG AAA                54
                                               Met Thr Val Lys
                                                 1

ACT GAG GCT GCT AAG GGC ACC CTC ACT TAC TCC AGG ATG AGG GGC ATG              102
Thr Glu Ala Ala Lys Gly Thr Leu Thr Tyr Ser Arg Met Arg Gly Met
  5              10                  15                  20

GTG GCA ATT CTC ATC GCT TTC ATG AAG CAG AGG AGG ATG GGT CTG AAC              150
Val Ala Ile Leu Ile Ala Phe Met Lys Gln Arg Arg Met Gly Leu Asn
                 25                  30                  35

GAC TTT ATT CAG AAG ATT GCC AAT AAC TCC TAT GCA TGC AAA CAC CCT              198
Asp Phe Ile Gln Lys Ile Ala Asn Asn Ser Tyr Ala Cys Lys His Pro
                 40                  45                  50

GAA GTT CAG TCC ATC TTG AAG ATC TCC CAA CCT CAG GAG CCT GAG CTT              246
Glu Val Gln Ser Ile Leu Lys Ile Ser Gln Pro Gln Glu Pro Glu Leu
         55                  60                  65

ATG AAT GCC AAC CCT TCT CCT CCA CCA AGT CCT TCT CAG CAA ATC AAC              294
Met Asn Ala Asn Pro Ser Pro Pro Pro Ser Pro Ser Gln Gln Ile Asn
         70                  75                  80

CTT GGC CCG TCG TCC AAT CCT CAT GCT AAA CCA TCT GAC TTT CAC TTC              342
Leu Gly Pro Ser Ser Asn Pro His Ala Lys Pro Ser Asp Phe His Phe
     85                  90                  95                 100
```

FIG. 1B

| | |
|---|---|
| TTG AAA GTG ATC GGA AAG GGC AGT TTT GGA AAG GTT CTT CTA GCA AGA<br>Leu Lys Val Ile Gly Lys Gly Ser Phe Gly Lys Val Leu Leu Ala Arg<br>                105                      110                    115 | 390 |
| CAC AAG GCA GAA GAA GTG TTC TAT GCA GTC AAA GTT TTA CAG AAG AAA<br>His Lys Ala Glu Glu Val Phe Tyr Ala Val Lys Val Leu Gln Lys Lys<br>                120                      125                    130 | 438 |
| GCA ATC CTG AAA AAG AAA GAG GAG AAG CAT ATT ATG TCG GAG CGG AAT<br>Ala Ile Leu Lys Lys Lys Glu Glu Lys His Ile Met Ser Glu Arg Asn<br>                135                      140                    145 | 486 |
| GTT CTG TTG AAG AAT GTG AAG CAC CCT TTC CTG GTG GGC CTT CAC TTC<br>Val Leu Leu Lys Asn Val Lys His Pro Phe Leu Val Gly Leu His Phe<br>                150                      155                    160 | 534 |
| TCT TTC CAG ACT GCT GAC AAA TTG TAC TTT GTC CTA GAC TAC ATT AAT<br>Ser Phe Gln Thr Ala Asp Lys Leu Tyr Phe Val Leu Asp Tyr Ile Asn<br>165                      170                      175                    180 | 582 |
| GGT GGA GAG TTG TTC TAC CAT CTC CAG AGG GAA CGC TGC TTC CTG GAA<br>Gly Gly Glu Leu Phe Tyr His Leu Gln Arg Glu Arg Cys Phe Leu Glu<br>                185                      190                    195 | 630 |

FIG. 1C

| | |
|---|---|
| CCA CGG GCT CGT TTC TAT GCT GCT GAA ATA GCC AGT GCC TTG GGC TAC<br>Pro Arg Ala Arg Phe Tyr Ala Ala Glu Ile Ala Ser Ala Leu Gly Tyr<br>             200                      205                  210 | 678 |
| CTG CAT TCA CTG AAC ATC GTT TAT AGA GAC TTA AAA CCA GAG AAT ATT<br>Leu His Ser Leu Asn Ile Val Tyr Arg Asp Leu Lys Pro Glu Asn Ile<br>             215                      220                  225 | 726 |
| TTG CTA GAT TCA CAG GGA CAC ATT GTC CTT ACT GAT TTC GGA CTC TGC<br>Leu Leu Asp Ser Gln Gly His Ile Val Leu Thr Asp Phe Gly Leu Cys<br>             230                      235                  240 | 774 |
| AAG GAG AAC ATT GAA CAC AAC AGC ACA ACA TCC ACC TTC TGT GGC ACG<br>Lys Glu Asn Ile Glu His Asn Ser Thr Thr Ser Thr Phe Cys Gly Thr<br>245                      250                      255                  260 | 822 |
| CCG GAG TAT CTC GCA CCT GAG GTG CTT CAT AAG CAG CCT TAT GAC AGG<br>Pro Glu Tyr Leu Ala Pro Glu Val Leu His Lys Gln Pro Tyr Asp Arg<br>                  265                      270                  275 | 870 |
| ACT GTG GAC TGG TGG TGC CTG GGA GCT GTC TTG TAT GAG ATG CTG TAT<br>Thr Val Asp Trp Trp Cys Leu Gly Ala Val Leu Tyr Glu Met Leu Tyr<br>             280                      285                  290 | 918 |
| GGC CTG CCG CCT TTT TAT AGC CGA AAC ACA GCT GAA ATG TAC GAC AAC<br>Gly Leu Pro Pro Phe Tyr Ser Arg Asn Thr Ala Glu Met Tyr Asp Asn<br>             295                      300                  305 | 966 |
| ATT CTG AAC AAG CCT CTC CAG CTG AAA CCA AAT ATT ACA AAT TCC GCA<br>Ile Leu Asn Lys Pro Leu Gln Leu Lys Pro Asn Ile Thr Asn Ser Ala<br>310                      315                      320 | 1014 |

FIG. ID

| | |
|---|---|
| AGA CAC CTC CTG GAG GGC CTC CTG CAG AAG GAC AGG ACA AAG CGG CTC<br>Arg His Leu Leu Glu Gly Leu Leu Gln Lys Asp Arg Thr Lys Arg Leu<br>325                    330              335              340 | 1062 |
| GGG GCC AAG GAT GAC TTC ATG GAG ATT AAG AGT CAT GTC TTC TTC TCC<br>Gly Ala Lys Asp Asp Phe Met Glu Ile Lys Ser His Val Phe Phe Ser<br>               345             350             355 | 1110 |
| TTA ATT AAC TGG GAT GAT CTC ATT AAT AAG AAG ATT ACT CCC CCT TTT<br>Leu Ile Asn Trp Asp Asp Leu Ile Asn Lys Lys Ile Thr Pro Pro Phe<br>          360              365             370 | 1158 |
| AAC CCA AAT GTG AGT GGG CCC AAC GAG CTA CGG CAC TTT GAC CCC GAG<br>Asn Pro Asn Val Ser Gly Pro Asn Glu Leu Arg His Phe Asp Pro Glu<br>        375            380            385 | 1206 |
| TTT ACC GAA GAG CCT GTC CCC AAC TCC ATT GGC AAG TCC CCT GAC AGC<br>Phe Thr Glu Glu Pro Val Pro Asn Ser Ile Gly Lys Ser Pro Asp Ser<br>    390              395            400 | 1254 |
| GTC CTC GTC ACA GCC AGC GTC AAG GAA GCT GCC GAG GCT TTC CTA GGC<br>Val Leu Val Thr Ala Ser Val Lys Glu Ala Ala Glu Ala Phe Leu Gly<br>405                    410             415             420 | 1302 |
| TTT TCC TAT GCG CCT CCC ACG GAC TCT TTC CTC TGAACCCTGT TAGGGCTTGG<br>Phe Ser Tyr Ala Pro Pro Thr Asp Ser Phe Leu<br>             425             430 | 1355 |

FIG. 1E

```
TTTTAAAGGA TTTTATGTGT GTTTCCGAAT GTTTTAGTTA GCCTTTTGGT GGAGCCGCCA      1415

GCTGACAGGA CATCTTACAA GAGAATTTGC ACATCTCTGG AAGCTTAGCA ATCTTATTGC      1475

ACACTGTTCG CTGGAATTTT TTGAAGAGCA CATTCTCCTC AGTGAGCTCA TGAGGTTTTC      1535

ATTTTTATTC TTCCTTCCAA CGTGGTGCTA TCTCTGAAAC GAGCGTTAGA GTGCCGCCTT      1595

AGACGGAGGC AGGAGTTTCG TTAGAAAGCG GACCTGTTCT AAAAAAGGTC TCCTGCAGAT      1655

CTGTCTGGGC TGTGATGACG AATATTATGA AATGTGCCTT TTCTGAAGAG ATTGTGTTAG      1715

CTCCAAAGCT TTTCCTATCG CAGTGTTTCA GTTCTTTATT TTCCCTTGTG GATATGCTGT      1775

GTGAACCGTC GTGTGAGTGT GGTATGCCTG ATCACAGATG GATTTGTTA TAAGCATCAA      1835

TGTGACACTT GCAGGACACT ACAACGTGGG ACATTGTTTG TTCTTCCAT ATTTGGAAGA       1895

TAAATTTATG TGTAGACTTT TTTGTAAGAT ACGGTTAATA ACTAAAATTT ATTGAAATGG      1955

TCTTGCAATG ACTCGTATTC AGATGCCTAA AGAAAGCATT GCTGCTACAA ATATTTCTAT     2015

TTTTAGAAAG GGTTTTTATG GACCAATGCC CCAGTTGTCA GTCAGAGCCG TTGGTGTTTT     2075

TCATTGTTTA AAATGTCACC TGTAAAATGG GCATTATTTA TGTTTTTTTT TTTGCATTCC     2135

TGATAATTGT ATGTATTGTA TAAAGAACGT CTGTACATTG GGTTATAACA CTAGTATATT     2195

TAAACTTACA GGCTTATTTG TAATGTAAAC CACCATTTTA ATGTACTGTA ATTAACATGG     2255

TTATAATACG TACAATCCTT CCCTCATCCC ATCACACAAC TTTTTTTGTG TGTGATAAAC     2315

TGATTTTGGT TTGCAATAAA ACCTTGAAAA ATAAAAAAAA AAAAAAAAAA AAAAA           2370
```

FIG. 2A

Met Thr Val Lys Thr Glu Ala Ala Lys Gly Thr Leu Thr Tyr Ser Arg
1              5                   10                  15

Met Arg Gly Met Val Ala Ile Leu Ile Ala Phe Met Lys Gln Arg Arg
            20                  25                  30

Met Gly Leu Asn Asp Phe Ile Gln Lys Ile Ala Asn Asn Ser Tyr Ala
            35                  40                  45

Cys Lys His Pro Glu Val Gln Ser Ile Leu Lys Ile Ser Gln Pro Gln
        50                  55                  60

Glu Pro Glu Leu Met Asn Ala Asn Pro Ser Pro Pro Ser Pro Ser
65                  70                  75                  80

Gln Gln Ile Asn Leu Gly Pro Ser Ser Asn Pro His Ala Lys Pro Ser
                85                  90                  95

Asp Phe His Phe Leu Lys Val Ile Gly Lys Gly Ser Phe Gly Lys Val
            100                 105                 110

Leu Leu Ala Arg His Lys Ala Glu Glu Val Phe Tyr Ala Val Lys Val
        115                 120                 125

Leu Gln Lys Lys Ala Ile Leu Lys Lys Lys Glu Glu Lys His Ile Met
        130                 135                 140

FIG. 2B

Ser Glu Arg Asn Val Leu Leu Lys Asn Val Lys His Pro Phe Leu Val
145 150 155 160

Gly Leu His Phe Ser Phe Gln Thr Ala Asp Lys Leu Tyr Phe Val Leu
165 170 175

Asp Tyr Ile Asn Gly Gly Glu Leu Phe Tyr His Leu Gln Arg Glu Arg
180 185 190

Cys Phe Leu Glu Pro Arg Ala Arg Phe Tyr Ala Ala Glu Ile Ala Ser
195 200 205

Ala Leu Gly Tyr Leu His Ser Leu Asn Ile Val Tyr Arg Asp Leu Lys
210 215 220

Pro Glu Asn Ile Leu Leu Asp Ser Gln Gly His Ile Val Leu Thr Asp
225 230 235 240

Phe Gly Leu Cys Lys Glu Asn Ile Glu His Asn Ser Thr Thr Ser Thr
245 250 255

Phe Cys Gly Thr Pro Glu Tyr Leu Ala Pro Glu Val Leu His Lys Gln
260 265 270

Pro Tyr Asp Arg Thr Val Asp Trp Trp Cys Leu Gly Ala Val Leu Tyr
275 280 285

FIG. 2C

Glu Met Leu Tyr Gly Leu Pro Pro Phe Tyr Ser Arg Asn Thr Ala Glu
    290                      295                  300

Met Tyr Asp Asn Ile Leu Asn Lys Pro Leu Gln Leu Lys Pro Asn Ile
305                310                315                320

Thr Asn Ser Ala Arg His Leu Leu Glu Gly Leu Leu Gln Lys Asp Arg
                325                330                335

Thr Lys Arg Leu Gly Ala Lys Asp Asp Phe Met Glu Ile Lys Ser His
        340                  345                350

Val Phe Phe Ser Leu Ile Asn Trp Asp Asp Leu Ile Asn Lys Lys Ile
        355                  360              365

Thr Pro Pro Phe Asn Pro Asn Val Ser Gly Pro Asn Glu Leu Arg His
    370                    375                380

Phe Asp Pro Glu Phe Thr Glu Glu Pro Val Pro Asn Ser Ile Gly Lys
385                390                395                400

Ser Pro Asp Ser Val Leu Val Thr Ala Ser Val Lys Glu Ala Ala Glu
            405                410                415

Ala Phe Leu Gly Phe Ser Tyr Ala Pro Pro Thr Asp Ser Phe Leu
            420                425              430

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 2370 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 43..1335

(xi) SEQUENCE DESCRIPTION: SEQ ID NO: 1:

```
CACGAGGGAG CGCTAACGTC TTTCTGTCTC CCCGCGGTGG TG ATG ACG GTG AAA        54
                                              Met Thr Val Lys
                                                1

ACT GAG GCT GCT AAG GGC ACC CTC ACT TAC TCC AGG ATG AGG GGC ATG      102
Thr Glu Ala Ala Lys Gly Thr Leu Thr Tyr Ser Arg Met Arg Gly Met
  5               10                  15                  20

GTG GCA ATT CTC ATC GCT TTC ATG AAG CAG AGG AGG ATG GGT CTG AAC      150
Val Ala Ile Leu Ile Ala Phe Met Lys Gln Arg Arg Met Gly Leu Asn
              25                  30                  35

GAC TTT ATT CAG AAG ATT GCC AAT AAC TCC TAT GCA TGC AAA CAC CCT      198
```

```
                                                                            -continued Asp Phe Ile Gln Lys Ile Ala Asn Asn Ser Tyr Ala Cys Lys His Pro
            40                  45                  50

GAA GTT CAG TCC ATC TTG AAG ATC TCC CAA CCT CAG GAG CCT GAG CTT        246
Glu Val Gln Ser Ile Leu Lys Ile Ser Gln Pro Gln Glu Pro Glu Leu
        55                  60                  65

ATG AAT GCC AAC CCT TCT CCT CCA CCA AGT CCT TCT CAG CAA ATC AAC        294
Met Asn Ala Asn Pro Ser Pro Pro Pro Ser Pro Ser Gln Gln Ile Asn
70                  75                  80

CTT GGC CCG TCG TCC AAT CCT CAT GCT AAA CCA TCT GAC TTT CAC TTC        342
Leu Gly Pro Ser Ser Asn Pro His Ala Lys Pro Ser Asp Phe His Phe
85                  90                  95                 100

TTG AAA GTG ATC GGA AAG GGC AGT TTT GGA AAG GTT CTT CTA GCA AGA        390
Leu Lys Val Ile Gly Lys Gly Ser Phe Gly Lys Val Leu Leu Ala Arg
                105                 110                 115

CAC AAG GCA GAA GAA GTG TTC TAT GCA GTC AAA GTT TTA CAG AAG AAA        438
His Lys Ala Glu Glu Val Phe Tyr Ala Val Lys Val Leu Gln Lys Lys
                120                 125                 130

GCA ATC CTG AAA AAG AAA GAG GAG AAG CAT ATT ATG TCG GAG CGG AAT        486
Ala Ile Leu Lys Lys Lys Glu Glu Lys His Ile Met Ser Glu Arg Asn
            135                 140                 145

GTT CTG TTG AAG AAT GTG AAG CAC CCT TTC CTG GTG GGC CTT CAC TTC        534
Val Leu Leu Lys Asn Val Lys His Pro Phe Leu Val Gly Leu His Phe
        150                 155                 160

TCT TTC CAG ACT GCT GAC AAA TTG TAC TTT GTC CTA GAC TAC ATT AAT        582
Ser Phe Gln Thr Ala Asp Lys Leu Tyr Phe Val Leu Asp Tyr Ile Asn
165                 170                 175                 180

GGT GGA GAG TTG TTC TAC CAT CTC CAG AGG GAA CGC TGC TTC CTG GAA        630
Gly Gly Glu Leu Phe Tyr His Leu Gln Arg Glu Arg Cys Phe Leu Glu
                185                 190                 195

CCA CGG GCT CGT TTC TAT GCT GCT GAA ATA GCC AGT GCC TTG GGC TAC        678
Pro Arg Ala Arg Phe Tyr Ala Ala Glu Ile Ala Ser Ala Leu Gly Tyr
                200                 205                 210

CTG CAT TCA CTG AAC ATC GTT TAT AGA GAC TTA AAA CCA GAG AAT ATT        726
Leu His Ser Leu Asn Ile Val Tyr Arg Asp Leu Lys Pro Glu Asn Ile
            215                 220                 225

TTG CTA GAT TCA CAG GGA CAC ATT GTC CTT ACT GAT TTC GGA CTC TGC        774
Leu Leu Asp Ser Gln Gly His Ile Val Leu Thr Asp Phe Gly Leu Cys
        230                 235                 240

AAG GAG AAC ATT GAA CAC AAC AGC ACA ACA TCC ACC TTC TGT GGC ACG        822
Lys Glu Asn Ile Glu His Asn Ser Thr Thr Ser Thr Phe Cys Gly Thr
245                 250                 255                 260

CCG GAG TAT CTC GCA CCT GAG GTG CTT CAT AAG CAG CCT TAT GAC AGG        870
Pro Glu Tyr Leu Ala Pro Glu Val Leu His Lys Gln Pro Tyr Asp Arg
                265                 270                 275

ACT GTG GAC TGG TGG TGC CTG GGA GCT GTC TTG TAT GAG ATG CTG TAT        918
Thr Val Asp Trp Trp Cys Leu Gly Ala Val Leu Tyr Glu Met Leu Tyr
                280                 285                 290

GGC CTG CCG CCT TTT TAT AGC CGA AAC ACA GCT GAA ATG TAC GAC AAC        966
Gly Leu Pro Pro Phe Tyr Ser Arg Asn Thr Ala Glu Met Tyr Asp Asn
            295                 300                 305

ATT CTG AAC AAG CCT CTC CAG CTG AAA CCA AAT ATT ACA AAT TCC GCA       1014
Ile Leu Asn Lys Pro Leu Gln Leu Lys Pro Asn Ile Thr Asn Ser Ala
        310                 315                 320

AGA CAC CTC CTG GAG GGC CTC CTG CAG AAG GAC AGG ACA AAG CGG CTC       1062
Arg His Leu Leu Glu Gly Leu Leu Gln Lys Asp Arg Thr Lys Arg Leu
325                 330                 335                 340

GGG GCC AAG GAT GAC TTC ATG GAG ATT AAG AGT CAT GTC TTC TTC TCC       1110
Gly Ala Lys Asp Asp Phe Met Glu Ile Lys Ser His Val Phe Phe Ser
                345                 350                 355
```

-continued

```
TTA ATT AAC TGG GAT GAT CTC ATT AAT AAG AAG ATT ACT CCC CCT TTT      1158
Leu Ile Asn Trp Asp Asp Leu Ile Asn Lys Lys Ile Thr Pro Pro Phe
            360                 365                 370

AAC CCA AAT GTG AGT GGG CCC AAC GAG CTA CGG CAC TTT GAC CCC GAG      1206
Asn Pro Asn Val Ser Gly Pro Asn Glu Leu Arg His Phe Asp Pro Glu
        375                 380                 385

TTT ACC GAA GAG CCT GTC CCC AAC TCC ATT GGC AAG TCC CCT GAC AGC      1254
Phe Thr Glu Glu Pro Val Pro Asn Ser Ile Gly Lys Ser Pro Asp Ser
    390                 395                 400

GTC CTC GTC ACA GCC AGC GTC AAG GAA GCT GCC GAG GCT TTC CTA GGC      1302
Val Leu Val Thr Ala Ser Val Lys Glu Ala Ala Glu Ala Phe Leu Gly
405                 410                 415                 420

TTT TCC TAT GCG CCT CCC ACG GAC TCT TTC CTC TGAACCCTGT TAGGGCTTGG    1355
Phe Ser Tyr Ala Pro Pro Thr Asp Ser Phe Leu
                425                 430

TTTTAAGGA TTTTATGTGT GTTTCCGAAT GTTTTAGTTA GCCTTTTGGT GGAGCCGCCA     1415

GCTGACAGGA CATCTTACAA GAGAATTTGC ACATCTCTGG AAGCTTAGCA ATCTTATTGC    1475

ACACTGTTCG CTGGAATTTT TTGAAGAGCA CATTCTCCTC AGTGAGCTCA TGAGGTTTTC    1535

ATTTTTATTC TTCCTTCCAA CGTGGTGCTA TCTCTGAAAC GAGCGTTAGA GTGCCGCCTT    1595

AGACGGAGGC AGGAGTTTCG TTAGAAAGCG GACCTGTTCT AAAAAAGGTC TCCTGCAGAT    1655

CTGTCTGGGC TGTGATGACG AATATTATGA AATGTGCCTT TTCTGAAGAG ATTGTGTTAG    1715

CTCCAAAGCT TTTCCTATCG CAGTGTTTCA GTTCTTTATT TTCCCTTGTG GATATGCTGT    1775

GTGAACCGTC GTGTGAGTGT GGTATGCCTG ATCACAGATG GATTTTGTTA TAAGCATCAA    1835

TGTGACACTT GCAGGACACT ACAACGTGGG ACATTGTTTG TTTCTTCCAT ATTTGGAAGA    1895

TAAATTTATG TGTAGACTTT TTTGTAAGAT ACGGTTAATA ACTAAAATTT ATTGAAATGG    1955

TCTTGCAATG ACTCGTATTC AGATGCCTAA AGAAAGCATT GCTGCTACAA ATATTTCTAT    2015

TTTTAGAAAG GGTTTTTATG GACCAATGCC CCAGTTGTCA GTCAGAGCCG TTGGTGTTTT    2075

TCATTGTTTA AAATGTCACC TGTAAAATGG GCATTATTTA TGTTTTTTTT TTTGCATTCC    2135

TGATAATTGT ATGTATTGTA TAAAGAACGT CTGTACATTG GTTATAACA CTAGTATATT     2195

TAAACTTACA GGCTTATTTG TAATGTAAAC CACCATTTTA ATGTACTGTA ATTAACATGG    2255

TTATAATACG TACAATCCTT CCCTCATCCC ATCACACAAC TTTTTTTGTG TGTGATAAAC    2315

TGATTTTGGT TTGCAATAAA ACCTTGAAAA ATAAAAAAAA AAAAAAAAA AAAAA          2370
```

(2) INFORMATION FOR SEQ ID NO: 2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Thr Val Lys Thr Glu Ala Ala Lys Gly Thr Leu Thr Tyr Ser Arg
 1               5                  10                  15

Met Arg Gly Met Val Ala Ile Leu Ile Ala Phe Met Lys Gln Arg Arg
            20                  25                  30

Met Gly Leu Asn Asp Phe Ile Gln Lys Ile Ala Asn Asn Ser Tyr Ala
        35                  40                  45

Cys Lys His Pro Glu Val Gln Ser Ile Leu Lys Ile Ser Gln Pro Gln
    50                  55                  60

Glu Pro Glu Leu Met Asn Ala Asn Pro Ser Pro Pro Pro Ser Pro Ser
```

```
                65                   70                   75                   80
            Gln Gln Ile Asn Leu Gly Pro Ser Ser Asn Pro His Ala Lys Pro Ser
                                85                   90                   95
            Asp Phe His Phe Leu Lys Val Ile Gly Lys Gly Ser Phe Gly Lys Val
                           100                  105                  110
            Leu Leu Ala Arg His Lys Ala Glu Glu Val Phe Tyr Ala Val Lys Val
                           115                  120                  125
            Leu Gln Lys Lys Ala Ile Leu Lys Lys Lys Glu Glu Lys His Ile Met
                           130                  135                  140
            Ser Glu Arg Asn Val Leu Leu Lys Asn Val Lys His Pro Phe Leu Val
            145                  150                  155                  160
            Gly Leu His Phe Ser Phe Gln Thr Ala Asp Lys Leu Tyr Phe Val Leu
                                165                  170                  175
            Asp Tyr Ile Asn Gly Gly Glu Leu Phe Tyr His Leu Gln Arg Glu Arg
                           180                  185                  190
            Cys Phe Leu Glu Pro Arg Ala Arg Phe Tyr Ala Ala Glu Ile Ala Ser
                           195                  200                  205
            Ala Leu Gly Tyr Leu His Ser Leu Asn Ile Val Tyr Arg Asp Leu Lys
                           210                  215                  220
            Pro Glu Asn Ile Leu Leu Asp Ser Gln Gly His Ile Val Leu Thr Asp
            225                  230                  235                  240
            Phe Gly Leu Cys Lys Glu Asn Ile Glu His Asn Ser Thr Thr Ser Thr
                                245                  250                  255
            Phe Cys Gly Thr Pro Glu Tyr Leu Ala Pro Glu Val Leu His Lys Gln
                           260                  265                  270
            Pro Tyr Asp Arg Thr Val Asp Trp Trp Cys Leu Gly Ala Val Leu Tyr
                           275                  280                  285
            Glu Met Leu Tyr Gly Leu Pro Pro Phe Tyr Ser Arg Asn Thr Ala Glu
                           290                  295                  300
            Met Tyr Asp Asn Ile Leu Asn Lys Pro Leu Gln Leu Lys Pro Asn Ile
            305                  310                  315                  320
            Thr Asn Ser Ala Arg His Leu Leu Glu Gly Leu Leu Gln Lys Asp Arg
                                325                  330                  335
            Thr Lys Arg Leu Gly Ala Lys Asp Asp Phe Met Glu Ile Lys Ser His
                           340                  345                  350
            Val Phe Phe Ser Leu Ile Asn Trp Asp Asp Leu Ile Asn Lys Lys Ile
                           355                  360                  365
            Thr Pro Pro Phe Asn Pro Asn Val Ser Gly Pro Asn Glu Leu Arg His
                           370                  375                  380
            Phe Asp Pro Glu Phe Thr Glu Glu Pro Val Pro Asn Ser Ile Gly Lys
            385                  390                  395                  400
            Ser Pro Asp Ser Val Leu Val Thr Ala Ser Val Lys Glu Ala Ala Glu
                                405                  410                  415
            Ala Phe Leu Gly Phe Ser Tyr Ala Pro Pro Thr Asp Ser Phe Leu
                           420                  425                  430

(2) INFORMATION FOR SEQ ID NO: 3:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: linear (ii) MOLECULE TYPE: peptide
```

-continued (xi) SEQUENCE DESCRIPTION: SEQ ID NO: 3:

Asp Pro Glu Phe Thr Glu Glu Pro Val Pro Asn Ser Ile Gly Lys Ser
1               5                   10                  15

Pro Asp Ser (2) INFORMATION FOR SEQ ID NO: 4:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Glu Ala Phe Leu Gly Phe Ser Tyr Ala Pro Pro Thr Asp Ser Phe Leu
1               5                   10                  15

CELL VOLUME-REGULATED HUMAN KINASE H-SGK

This application is a Divisional of application Ser. No. 09/031,295, filed Feb. 26, 1998 now U.S. Pat. No. 6,326,181 issued Dec. 4, 2001.

BACKGROIND OF INVENTION

The present invention relates to the cloning and characterization of a human serine/threonine kinase (h-sgk: serum and glucocorticoid dependent kinase). The invention furthermore relates to reagents for diagnosing conditions associated with a change in cell volume and/or in "macromolecular crowding" in the body, such as, for example, hypernatremia, hyponatremia, diabetes mellitus, renal failure, hypercatabolism, hepatic encephalopathy, inflammation and microbial or viral infections. The present invention additionally relates to pharmaceuticals comprising the h-sgk, nucleic acids which code for the h-sgk, or receptors, in particular antibodies, which specifically bind to the h-sgk.

Even when the extracellular osmolarity is constant, the constancy of the cell volume is continuously challenged due to transport across cell membranes and cellular metabolism, i.e. production and breakdown of osmotically active substances.

Cell swelling and shrinkage disturb the intracellular environment by diluting and concentrating, respectively, cellular macromolecules which lead to extensive impairment of cellular functions. This is why cells have developed a large number of cell volume-regulating mechanisms. Cell swelling leads, in most tissues, to cellular release of ions due to activation of ion channels and KCl cotransport. Cell shrinkage conversely leads to cellular uptake of ions due to activation of NaCl/KCl cotransporter and $Na^+/H^+$ exchanger.

Furthermore, cell shrinkage stimulates cellular accumulation and cell swelling stimulates cellular release of osmolytes, molecules which are specifically used to generate intracellular osmolarity [Burg, M. B., Am. J. Physiol. 268: F983–F996, 1995].

Finally, changes in the liver cell volume influence hepatocellular metabolism and gene expression [Häussinger et al. (1994) Am. J. Physiol. 267, E343–E355]. Cell swelling acts like an anabolic signal which stimulates protein and glycogen synthesis and inhibits protein and glycogen breakdown. Conversely, cell shrinkage acts as a catabolic signal by promoting the breakdown of glycogen and proteins and inhibiting the synthesis of proteins and glycogen [Häussinger et al. (1994) Am. J. Physiol. 267, E343–E355].

The cell volume has been recognized as a crucial element in the regulation of hepatocellular metabolism by hormones, cellular amino acid uptake and oxidative stress.

The signal mechanisms which couple cell function to the changes in the cellular hydration state are substantially unknown. Changes in the cell volume achieve their various effects on cell function partly by stimulating or suppressing the expression of particular genes, whose products then influence the expression or activity of a large number of cell components. In order to discover genes which are increasingly expressed on cell swelling, we carried out a differential mBNA fingerprinting assay on cDNAs from hepatocytes which had been exposed either to isotonic or to anisotonic extracellular fluid. This resulted in a plurality of bands which showed differential expression rates on use of different primers.

It has been found, surprisingly, that the expression of one of these bands was stimulated under hypertonic conditions and inhibited under hypotonic conditions. The cDNA sequence of this band, whose expression is influenced in a particular way by changes in cell volume, has been analyzed in detail. It was found by sequence comparison that there is no similarity with any previously known human gene. The gene which has been found, whose nucleotide sequence is depicted in FIG. 1, surprisingly codes for a kinase, a putative serine/threonine kinase. Its sequence is depicted in FIG. 2 as well as in FIG. 1. It is highly homologous with previously known rat sgk (serum and glucocorticoid dependent kinase), a kinase whose expression is increased by serum and glucocorticoids. A dependence of the rat sgk on cell volume has not previously been described, however.

The present invention accordingly relates to a human cell volume-regulated kinase (h-sgk) and to processes for producing it by genetic manipulation.

Expression of the h-sgk is greatly dependent on the cell volume. Cell swelling inhibits expression of the h-sgk, whereas cell shrinkage stimulates expression of the h-sgk. Furthermore, expression of the h-sgk is inhibited by urea. Urea impairs, like changes in cell volume, the stability and thus the function of cellular proteins and the packing density of the cellular macromolecules, called macromolecular crowding [Minton, A. P., Mol. Cell. Biochem. 55: 119–140, 1983]. h-sgk expression is therefore a measure of the cellular macromolecular crowding. Transcription of the h-sgk is not, in contrast to rat sgk, influenced either by corticoids or by fetal calf serum (FCS), however.

The h-sgk is expressed in a large number of human tissues such as liver, heart, pancreas, muscle, kidney, lung, placenta, lymphocytes and several structures in the brain (hippocampus, nucleus caudatus, corpus callosum, substantia nigra, nucleus subthalamicus and thalamus).

It has emerged that the h-sgk has a considerable diagnostic potential for many diseases in which changes in cell volume play a crucial pathophysiological part. Expression of the h-sgk can be demonstrated by detecting and/or quantifying the mRNA by using suitable probes, for example in a Northern blot or by in situ hybridization, and the h-sgk itself can be detected, for example, using suitable antibodies in a Western blot or by immunohistochemistry. Suitable probes and antibodies have already been successfully checked for utilizability.

The present invention therefore also relates to the diagnostic use of the h-sgk, its fragments or the relevant nucleic acids coding therefor. The diagnostic techniques which can be used are known to the skilled worker. These may be all immunoassay formats known from the prior art, such as, for example, Western blot or enzyme linked immunosorbent assay (ELISA), but also homogeneous assay formats not bound to a solid phase. Conceivable examples are competitive assay variants, but also indirect assays or designs on the sandwich principle are also directly possible. It is likewise possible to employ the labeling techniques known to the skilled worker. All types of nucleic acid detection techniques can be used, such as, for example, Southern blot, Northern blot and all variants of the hybridization techniques, including in situ hybridization.

The h-sgk can be detected both in body fluids, for example, blood, plasma or serum, and in solid tissues, for example biopsy material. Detection of the h-sgk is indicated wherever changes in the cell volume or in the macromolecular crowding in the body occur, such as in hypernatremia, hyponatremia, diabetes mellitus, renal failure, hypercatabolism, hepatic encephalopathy, inflammation and infections.

Furthermore, dysfunction of the h-sgk might lead to impaired regulation of hepatic metabolism. Detection of the h-sgk would therefore be useful for diagnostic elucidation of fructose intolerance and hyper- and hypoglycemic states.

Hypernatremia: This is a life-threatening disturbance which occurs, for example, when there is osmotic diuresis and water diuresis due to central or nephrogenic diabetes insipidus. Central diabetes insipidus results from a genetic defect, craniocerebral trauma, damage to hypothalamic neurons due to inflammations, hypoperfusion, tumors, consumption of alcohol, opiates and some drugs. Nephrogenic diabetes insipidus results from genetic defects, hypokalemia, hypercalcemia, protein deficiency, pyelonephritis, and treatment with various drugs etc. As is shown in experiments on cultivated liver and kidney cells, an increase in the extracellular $Na^+$ concentration, which is always associated with an increase in the extracellular osmolarity too, results in increased expression of the h-sgk. The kinase can thus be used as indicator of the extent of cell shrinkage and be employed for monitoring the therapy. Surveillance of this type is important inasmuch as fatal cell swelling may occur on occasion if the correction of hypernatremia is too rapid, despite extracellular hyperosmolarity.

Hyponatremia: Hyponatremia below 130 mmol/l is found in about 1–2% of all hospitalized patients. The causes of this life-threatening disturbance are diabetes mellitus, ketonuria, hepatic insufficiency, diuretics, opiates, various drugs, osmotic diuresis, bicarbonaturia, adrenal insufficiency, salt-loss nephritis, nephrotic syndrome, increased secretion of ADH and losses of isotonic fluid (for example diarrhea) with replacement only of water. If the hyponatremia is the result of an increase in other osmolytes in the blood, then the cell volume and expression of the h-sgk remain normal. However, if the hyponatremia reflects a hypoosmolarity with cell swelling, then there is a reduction in h-sgk expression.

Thus, measurement of the h-sgk provides information about the presence of cell swelling and allows a rational decision to be made about the therapeutic procedure. The kinase can be employed to check progress during therapy. Correction of hyponatremia which is too rapid may result in cell shrinkage, which is occasionally fatal.

Diabetes mellitus: Hyperglycemia occurs in diabetes mellitus and results in an increase in the extracellular osmolarity and thus causes cell shrinkage. The glucose undergoing glomerular filtration exceeds the maximum renal transport rate and, in this way, forces osmotic diuresis, in which $Na^+$ and water are lost. This may result in development of hyponatremia. The increased extracellular osmolarity and the oversupply of glucose promote the cellular production of sorbitol which, when the extracellular osmolarity falls, results in cell swelling. The cell shrinkage and cell swelling associated with diabetes mellitus are ascribed crucial importance in the pathophysiology [McManus et al., New England J. Med. 333: 1260–1266, Dermadash et al., Kidney intern. 50: 2032–2040, 1996]. Measurement of the h-sgk in a patient with diabetes mellitus permits the changes in cell volume to be estimated and thus provides a solid basis for compensating electrolyte disturbances. In this case too, observation of the progress can prevent excessive corrections.

Renal failure: In renal failure there is a massive increase in the urea concentration to levels which have a destabilizing effect on proteins, cause cells to shrink and bring about a decrease in h-sgk expression. The destabilizing effect of urea is diminished by the formation of trimethylamines. When the changes in the urea concentration are rapid, the accumulation of trimethylamines cannot keep up, and disturbances of cellular metabolism are to be expected owing to the changes in cell volume. Determination of the h-sgk may reveal an imbalance between destabilizing urea and stabilizing trimethylamines. Therapeutic administration of trimethylamines would, where appropriate, be indicated if the h-sgk is greatly depressed.

Hypercatabolism: In a number of catabolic states, such as sepsis, burns, acute pancreatitis, major operations, changes in the volume of muscle cells correlating with the extent of hypercatabolism have been detected. Cell shrinkage in fact leads to enhancement, and cell swelling to inhibition, of proteolysis. Determination of the h-sgk might justify in the individual case the use of therapeutic measures suitable for counteracting cell shrinkage, such as administration of glutamine [Haussinger et al., Lancet, 341: 1330–1332, 1993] or of osmolytes [Burg, M. B., J. Exp. Zool. 268(2): 171–5, 1994].

Hepatic encephalopathy: There is compelling evidence that hepatic encephalopathy is brought about by swelling of glial cells [Norenberg, M. D., Exp. Neurol. 53(3): 213–220, 1994]. It is in fact possible to detect a decrease in the osmolyte inositol in the brain in cases of liver disease [Kreis et al., NMR Biomed. 4: 109–116, 1991]. Complete disappearance coincides with the onset of encephalopathy. Development and use of suitable substrates for the h-sgk might allow the h-sgk activity in the brain to be measured and counter-regulated even before the encephalopathy occurs. Where appropriate, h-sgk expression in more readily accessible tissues might also be used as indicator of volume changes in glial cells.

Alzheimer disease: Recent evidence points to increase of peripheral cell volume in Alzheimer disease. Moreover, the osmolyte inositol is enhanced in patients with Alzheimer disease, but not in dementia of other causes. H-sgk expression may contribute to diagnosis of Alzheimer disease.

Infections/Inflammation: Sepsis is associated with extensive cell shrinkage [Haussinger et al., Lancet 1993, 341: 1330–1332] with the corresponding occurrence of hypercatabolism. In fact, the cell volume plays an important part in the pathogen-host relationship. Expression of the h-sgk might be a valuable parameter for assessing the pathophysiology of infections. In situ hybridisation reveals marked increase of tissue levels of h-sgk in inflammatory diseases, such as hepatitis, pancreatitis, Morbus Crohn, or glomerulonephritis. Moreover, h-sgk expression is enhanced by TGFβ which has been implicated in progressive fibrosis such as liver cirrhosis, lung fibrosis and progressive renal failure. H-sgk expression has indeed been found enhanced in patients with chronic renal failure.

Hyperglycemia/hypoglycemia/lactacidosis: Diminished or enhanced expression and/or function of the h-sgk might result in disturbances of carbohydrate metabolism as observed in association with cell shrinkage and cell swelling [Lang et al., Pflügers Arch. 413: 209–216, 1989]. A diminished function would result in the threat of hypoglycemia. Enhanced function might be followed, on the one hand, by hyperglycemia or, on the other hand, by lactacidosis. Thus, in the diagnostic elucidation of hyperglycemia, hypoglycemia and lactacidoses of unclear origin, it would always also be expedient to investigate the expression and function of the h-sgk.

The present invention is additionally explained further by the following detailed description and, furthermore, described by the examples and the claims.

BRIEF DESCRIPTION OF THE INVENTION

FIGS. 1A–1E disclose the nucleotide sequence encoding the human cell volume-regulated kinase h-sgk. This sequence corresponds to SEQ ID NO: 1 in the sequence listing.

FIGS. 2A–2C disclose the amino acid sequence of the human cell volume-regulated kinase h-sgk. This sequence corresponds to SEQ ID NO: 2 in the sequence listing.

DETAILED DESCRIPTION IF THE INVENTION

Materials and Methods

Materials: Fetal calf serum and DMEM (Dulbecco's modified Eagle's medium) were purchased from GIBCO/BRL (Eggenstein, Germany), enzymes from STRATAGENE (Heidelberg, Germany) and BOEHRINGER MANNHEIM (Mannheim, Germany), α-[$^{35}$S]-dATP from ICN (Eschwege, Germany), SuperScript® reverse transcriptase from GIBCO/BRL. PCR® (polymerase chain reactions) were carried out in a Crocodile® II thermocycler (APPLIGENE ONCOR, Heidelberg, Germany) using Prime Zyme® DNA polymerase and PCR buffer from BIOMETRA (Göttingen, Germany). RAP-PCR primers were purchased from STRATAGENE, and sequencing primers from MWG (Ebersberg, Germany). Manual sequencing was carried out on an S2 sequencer from GIBCO/BRL using the Fidelity® DNA sequencing system (APPLIGENE ONCOR).

Cell culture: HepG2 human hepatoma cells were cultivated in Dulbecco's modified Eagle's medium (DMEM) with 5% $CO_2$, 5 mM glucose, pH 7.4, which was supplemented with 10% (vol/vol) fetal calf serum (FCS) at 37° C. Before the RNA isolation, the cells were cultivated to 90% confluence and kept in basal medium Eagle's (BME, GIBCO/BRL) without fetal calf serum for 12 hours. The extracellular osmolarity was varied by adding or removing defined amounts of sodium chloride without changing the other components of the BME medium. In experiments to test the effects of amino acids, the cells were kept in an extracellular solution free of amino acids for two hours before adding the amino acids.

RAP-PCR: RNA fingerprinting PCR (RAP-PCR) was carried out as described previously [McClelland et al., 1994, Nucleic Acids Res. 22, 4419–4431]. After electrophoresis through a 4% acrylamide/7 M urea polyacrylamide gel, the PCR products were visualized by silver staining [Sanguinetti et al., Biotechniques 17, 914–921, 1994]. All the bands which were visible only under one condition (hypertonic or hypotonic) were subsequently confirmed by reverse transcription and PCR with RNA from new cultures. The RAP-PCR was carried out with four different primer pairs for the cDNA synthesis and PCR amplification. In addition, different temperatures between 30° C. and 40° C. were chosen in the first amplification round. Together with these modifications, a total of 64 PCR runs were carried out.

Isolation of the bands: Bands which showed reproducible differences were cut out under sterile conditions. The amplicon was eluted in 100 μl of buffer (50 mM KCl, 10 mM TRIS-Cl pH 9.0, 0.1% Triton ×100) at 70° C. overnight. Reamplification by PCR was carried out with 3.0 μl of eluate using suitable primers (250 nM), 200 μM dNTP, 1× low-salt buffer (STRATAGENE) with 1.5 mM $MgCl_2$ and 5 units of Taq+® DNA polymerase (STRATAGENE) with the following temperature cycle profiles: one cycle at 95° C. for 60 sec, 30 cycles at 95° C. (15 sec), 55° C. (15 sec), 72° C. (60 sec) and finally at 72° C. for 5 minutes. After confirmation by PAGE that only one defined amplicon having the expected length had been produced, this amplicon was used directly for forming the probe.

Northern analysis: Digoxigenin (DIG)-coupled probes were produced by direct PCR labeling of the various amplicons using the suitable primers and the conditions as described above apart from the fact that the following dNTP concentrations were used: 200 μM dATP, 200 μM dCTP, 200 μM dGTP, 190 μM dTTP and 10 μM DIG-dUTP (BOEHRINGER). Northern blots were prepared using 20 μg of total RNA or 2 μg of poly(A)-RNA, which had been separated by electrophoresis through 1% agarose gels in the presence of 2.2 M formaldehyde. Equivalent loading of probes in the investigation of poly(A)-RNA was checked by ethidium bromide staining of ribosomal RNA bands or by DIG-labeled antisense RNA probe using the human heterogeneous nuclear ribonucleoprotein C1 as internal standard. The size of the RNA was estimated using the DIG-labeled molecular weight marker I (BOEHRINGER). Vacuum blotting (APPLIGENE ONCOR Trans DNA Express Vacuum Blotter) was used for transfer to positively charged nylon membranes (BOEHRINGER) which were then crosslinked by ultraviolet light (STRATAGENE UV Stratalinker® 2400). Hybridization was carried out in DIG-Easy-Hyb® (BOEHRINGER) with a probe concentration of 25 ng/ml or 100 ng/ml at 50° C. or 65° C. for DNA probes or RNA probes overnight. Probes which showed different expression were subcloned using the pCR-Script SK(+) cloning kit (STRATAGENE) and checked in Northern blots. The Northern blots which are shown hereinafter were derived from these subclones.

Other methods: DNA sequencing of the pCR clone was carried out with the Fidelity® DNA sequencing system (APPLIGENE ONCOR). Sequencing products were labeled with α-[$^{35}$S]-dATP and fractionated on a 6% polyacrylamide/8 M urea sequencing gel. The GenBank data were scanned for homologous sequences using the FASTA computer program [Pearson, W. R. & Lipman, D. J. (1988) Proc. Natl. Acad. Sci. USA 85, 2444–2448]. The sequence of the complete h-sgk cDNA was obtained with the aid of the I.M.A.G.E. consortium clone ID 42669 from the TIGR/ATCC special collection of human cDNA clones. The gene data were examined with the aid of the European Molecular Biology Laboratory EMBL (Heidelberg), the BLAST network service and—for the protein alignments—the BLITZ server on the newest edition of the SwissProt protein database.

Nucleotide sequence accession number: The h-sgk cDNA sequence, SEQ ID NO:1, was entered into the GenBank database under accession number Y10032 and was inaccessible until Mar. 27, 1997.

Results

Differential gene expression in HepG2 cells in hypotonic, isotonic and hypertonic extracellular fluid: mRNA was isolated from HepG2 cells which had been pretreated for 1 or 2 hours with hypotonic (hypotonic I: minus 100 mosmol/l due to removal of 50 mM NaCl and hypotonic II: minus 50 mosmol/l due to removal of 25 mM NaCl compared with isotonic control medium), isotonic (with total osmolarity of 290 mosmol/l and an NaCl concentration of 114 mM) or hypertonic (plus 50 mosmol/l by addition of 50 mM raffinose) medium. The mRNA was used as template for the RAP-PCR with arbitrary primers. The products of the RAP-PCR were loaded onto denatured polyacrylamide gels and fractionated in parallel lanes for comparison. Several bands showed differential expression on use of several primers. Four differential bands from the RAP-PCR gels were analyzed further: two proved in the subsequent Northern blot analysis to be false-positive, one band was enhanced by hypotonic and hypertonic conditions but its sequence showed no similarity with any previously known cloned gene. One band of about 500 base pairs showed increasing expression with increasing extracellular osmolarity (hypotonic I-hypotonic II-isotonic-hypertonic). This band was purified from the gel and reamplified using the primer RAP-A4. After PCR labeling with digoxigenin, Northern blots were made using this amplicon in order to confirm differential expression in various cell preparations which had been pretreated for two hours with hypotonic I, isotonic and hypertonic medium.

A single transcript of about 2.6 kilobases was greatly influenced by the changes in the extracellular osmolarity (FIGS. 1A–1E). The amount of transcript was reduced when the osmolarity decreased and was enhanced when the osmolarity increased.

Cloning and sequencing of the differentially regulated h-sgk gene. The PCR product with a length of 500 base pairs was subcloned into the PCR II vector, and a new probe was produced with this construct in order to demonstrate identity between the original and the subcloned DNA fragment. Rehybridization of a Northern blot using this probe led to identical results as with the original probe. In addition, a Southern blot analysis was carried out with the new construct and hybridized with the original construct. Strong hybridization after two high-stringency washes confirmed the identity of the sequence.

Sequence analyses in both directions showed the presence of the primers used on both sides of the amplicon. An amino acid sequence translated by one reading frame of the nucleotide sequence showed 95% identity with the carboxyl-terminal amino acid sequence of the rat sgk (serum and glucocorticoid regulated protein kinase), a new member of the serine/threonine protein kinase protein family which was cloned from a rat mammary gland tumor cell line [Webster et al., Mol. Cell. Biol. 13, 2031–2040, 1993a]. Because of the great similarity, the name h-sgk (human) was chosen for the new protein.

The Genbank database was scanned for similar human sequences using the FASTA computer program. Several EST (Expressed Sequence Tags) DNA sequences from the TIGR/ATCC special collection of human cDNA clones showed 100% sequence agreement with parts of the h-sgk cDNA fragments. After multiple alignments of 30 different TIGR/ATCC human cDNA clones with the rat sgk cONA sequence (Genbank accession number L01624) and with the h0sgk DNA fragment, it was assumed that the I.M.A.G.E. consortium construct with the clone ID 42669 from a human infantile brain library has the complete coding sequence of the h-sgk. Sequence analysis of this construct with coinciding sequences in th sense and antisense directions revealed a cDNA sequence of about 2.4 kilobases. In order to demonstrate involvement of the complete h-sgk, the 5' end of the clone (nucleotides 1-285 of the coding sequence) was subcloned into the pCR II vector and hence a new probe was produced with this construct. Hybridization of a Northern blot with this probe resulted in identical results as with the original probes (FIGS. 1A–1E). The longest reading frame in the clone investigated (1.3 kb) afforded a 431 amino acid protein with an overall identity of 98% with the rat sgk protein.

Regulation of h-sgk expression by changing the extracellular osmolarity: In order to investigate the effect of changes in the extracellular osmolarity on the amounts of h-sgk transcript, HepG2 cells were incubated for various times in hypotonic (190 mol/l), isotonic (290 mosmol/l) and hypertonic (390 mosmol/l) BME medium without FCS. The h-sgk mRNA concentrations increased greatly within 60 min in hypertonic solution. The initial rise was evident within 30 minutes and reached a maximum within two hours. Induction of the h-sgk therefore directly follows the change in the osmolarity. The transcript concentrations increased further over 4 to 8 hours in hypertonic extracellular BME medium, and then gradually fell again over the course of the next 16 to 24 hours to the initial concentrations. On the other hand, the h-sgk transcript concentrations decreased rapidly in hypotonic extracellular solution, the decrease being evident after only 30 minutes and reaching a maximum within two hours.

Different osmolarities (140, 190, 240, 290, 340, 390 and 440 mosmol/l) showed differences in the expression of the h-sgk within two hours. A steep correlation of h-sgk expression with the extracellular osmolarity was detectible over the entire range. A 30% increase in osmolarity was associated with an approximately tripling of kinase expression. An increase in osmolarity from 290 to 340 mosmol/l, and a decrease in concentration from 290 to 240 mosmol/l, induced significant changes in h-sgk expression. The transcriptional control mechanism thus evidently reacts very sensitively to changes in osmolarity. Induction of h-sgk RNA was independent of de novo protein synthesis. The increase in the transcript concentration in hypertonic BME medium is5 greater in the presence of the protein synthesis inhibitor cycloheximide (10 $\mu$g/ml) than in the absence of the inhibitor.

The rapid decrease in the h-sgk transcript concentrations immediately after reducing the extracellular osmolarity suggests that the h-sgk mRNA has a short half-life. In order to investigate the rate of decrease of the h-sgk transcript concentrations, HepG2 cells were treated with hypertonic medium (390 mosmol/l) for two hours in order to obtain a maximum increase in the h-sgk transcript concentrations. Then some of the cells were exposed to the RNA polymerase inhibitor actinomycin D (5 $\mu$g/ml), and the remaining cells to hypotonic medium (190 mosmol/l). After various times, RNA was prepared and the transcript concentrations of the two groups of cells were compared. Actinomycin D treatment resulted in a rapid decrease in the h-sgk transcript concentrations with an estimated half-life of about 30 minutes. Treatment of the cells with hypotonic extracellular medium resulted in an equally rapid decrease in the transcript concentrations.

Regulation of h-sgk transcript concentrations by isotonic changes in cell volume. In order to be able to distinguish between the effects of changes in the cell volume, the ionic strength and the osmolarity, the cell volume was manipulated by two different methods while keeping the ionic strength and osmolarity the same.

Within two hours of isotonic cell shrinkage due to inhibition of the NaCl/KCl cotransporter and of the $Na^+/H^+$ exchanger with bumetanide and 3-methylsulfonyl-4-(1-piperidino)benzoylguanidine (EP-0 416 499) there was an increase in h-sgk expression, an effect which was further enhanced by additionally increasing the extracellular osmolarity. Cell swelling by offering various amino acids (amino acid mixture of 1×BME amino acids, GIBCO/BRL) conversely resulted within two hours in a decrease in h-sgk transcript concentrations. It is thus the cell volume, not the osmolarity or the ionic strength, which regulates h-sgk expression.

In order to check whether expression of h-sgk in HepG2 cells is, similar to the rat sgk in mammary gland tumor cells [Webster, M. K. (1993) Mol. Cell. Biol. 13, 2031–2040], regulated by glucocorticoids or fetal calf serum (FCS), HepG2 cells were incubated with dexamethasone (1 $\mu$M) or with FCS (10%) for two to 12 hours. No effect of glucocorticoids or FCS on the h-sgk transcript concentrations in HepG2 cells could be found in Northern blots.

Regulation of sgk transcript concentrations by the extracellular osmolarity in Madin Darby canine kidney (MDCK)

cells. In order to check whether the observed dependence of h-sgk expression on cell volume is a peculiarity of HepG2 cells, the canine kidney epithelial cells MDCK were exposed to hypotonic (190 mosmol/l) and hypertonic (390 mosmol/l) BME medium for two hours. It was possible to detect h-sgk transcripts with a length of about 2.6 kilobases even after several high-stringency washing steps with 0.5× SSC (standard saline citrate) at 65° C., indicating great homology of the sgk gene sequences between different species.

Changes in the extracellular osmolarity had a similar effect on the transcript concentrations in MDCK cells as in HepG2 cells.

Tissue-specific expression of h-sgk. A premade Multiple Tissue Northern Blot (CLONTECH, Heidelberg, Germany) was investigated with the h-sgk DNA probe. Expression of h-sgk shows a certain tissue specificity, with greatest expression in pancreas, liver and myocardium. Expression is somewhat less in placenta, lung and skeletal muscle. There is low but detectable expression in brain and kidney. In human brain tissue, expression is greatest in the substantia nigra and the corpus callosum, average in the corpora amygdala, hippocampus, nucleus caudatus and nucleus subthalamicus, and least in the thalamus. It is of interest that a second transcript of 7 kilobases was found in almost all tissues, with greatest expression in the pancreas. This transcript is possibly another h-sgk mRNA due to alternative splicing or a gene homologous to h-sgk. The 7 kilobase transcript had not been found in HepG2 Northern blots.

Regulation of h-sgk expression by urea. The presence of urea in the extracellular space depresses h-sgk expression. The diminution in h-sgk expression was moderate at 50 mmol/l urea and extensive with 100 mmol/l urea.

Discussion

The human gene h-sgk, whose transcription is regulated by changes in the cell volume, codes for a putative serine/threonine protein kinase with great homology with the sequence of rat sgk, which has recently been described as serum- and glucocorticoid-regulated gene from rat mammary gland tumor cells, as lesion-induced gene after CNS lesions in the rat brain [Imaizumi et al., Mol. Brain Res. 26, 189–196, 1994] and as gene induced by testosterone and follicle stimulating hormone in granulosa cells of the rat ovary [Richards et al., Recent Prog. Horm. Res. 50, 223–254, 1995]. The 49 kD h-sgk protein shows approximately 98% homology with the rat sgk protein with substantially conservative amino acid exchanges. It exhibits about 50% homology in its catalytic domain with several kinases of the second messenger family, such as rac protein kinase, protein kinase C, ribosomal protein S6 kinase, and cAMP-dependent protein kinase [Webster et al., (1993b) J. Biol. Chem. 268, 11482–11485, Webster et al. (1993a) Mol. Cell. Biol. 13, 2031–2040].

The level of expression of the 2.6 kilobase h-sgk transcript in HepG2 cells is greatly influenced by changes in the extracellular osmolarity. Increased transcript concentrations were found within 30 minutes after the extracellular osmolarity was increased. This induction was independent of de novo protein synthesis. The transcript concentrations fall within 30 minutes after the extracellular osmolarity is reduced. The decrease was as rapid as the fall after inhibition of transcription by actinomycin D.

Changes in cell volume accordingly influence the h-sgk transcription rate. The reduced h-sgk transcription rate after osmotic cell swelling and the short half-life ensure rapid and efficient relation of h-sgk RNA transcript concentrations in HepG2 cells.

Isosmotic changes in the cell volume influence h-sgk expression in the same way. Cell shrinkage was achieved by inhibiting the essential ion transport mechanisms of the $Na^+/H^+$ exchanger and NaCl/KCl cotransporter by their specific blockers 3-methylsulfonyl-4-(1-piperidino)-benzoylguanidine (EP-0 416 499) and bumetanide. Cell swelling was brought about by adding amino acids and the subsequent hepatocellular accumulation of the amino acids via $Na^+$-dependent amino acid transporters such as, for example, system A, N, and ASC. The transcript concentrations correlated with the cell volume, not with the osmolarity.

After long-lasting osmotic cell shrinkage, the transcript concentrations increased steeply within the first half hour and then remained elevated for 8 hours before they gradually declined again. This long-lasting increase is apparently contradictory to the rapidity of cell volume regulation. Liver cells which have been shrunk or swollen osmotically do not, however, regulate their cell volume completely but still remain moderately shrunken or swollen after the rapid phase of volume regulation [Häussinger et al., (1994) Am. J. Physiol. 267, E343-E355].

The remaining changes in cell volume might be responsible for the altered h-sgk expression.

Besides the cell volume itself, urea has a great effect on h-sgk expression. Urea exerts a destabilizing action on proteins and, in this way, imitates the effect of cell swelling. The h-sgk would thus be a sensor of protein stability or of the packing density of the cellular macromolecules. The destabilizing effect of urea is diminished by the formation of trimethylamines, whereby the destabilizing effect of urea is probably diminished in cases of renal failure.

The cellular effects of h-sgk are still uncertain. In particular, it is not yet possible at present to state with certainty whether the effects of h-sgk are involved in cell volume regulation. However, the effect of h-sgk is immaterial for use of h-sgk as diagnostic aid.

Despite the evident homology with the rat sgk sequence, we were unable to find any parallels to the regulation of the rat sgk. Neither serum (FCS) nor glucocorticoids (dexamethasone), both of which had showed a strong effect on sgk transcription in rat mammary gland tumor cells, affected h-sgk expression in HepG2 cells. It therefore appears that different h-sgk promoter sequences regulate expression of the protein in the various types of cells. Thus it is conceivable that h-sgk expression is not regulated exclusively by the cell volume or the packing density. We were also able to detect a dependence of h-sgk expression on cell volume in kidney epithelial cells (MDCK) and in macrophages. The dependence of h-sgk expression on cell volume is thus not peculiar to HepG2 cells. The h-sgk 5'-flanking sequences in the various cells might uncover the regulating elements responsible for differences in sgk transcript expression. Like the previously described glucocorticoid- and serum-induced expression of sgk in the rat, the cell volume-induced expression of h-sgk RNA takes only 30 minutes. The half-life of 30 minutes for the h-sgk transcripts in HepG2 cells is just as short as the sgk half-life in rat mammary gland tumor cells, as shown by the experiments with the RNA polymerase inhibitor actinomycin D.

The h-sgk transcript is expressed in all human tissues investigated to date. Expression is particularly great in pancreas and liver, possibly because of the specialized epithelial function of these tissues.

Protein phosphorylation is a rapid and reversible mechanism for converting signals from the extracellular space into alterations of a large number of cell functions. The h-sgk protein kinase might induce, by phosphorylating specific proteins, some of the mechanisms regulating cell volume and represent a previously unknown link between cellular hydration and cell function.

EXAMPLES

1. Procedure for Northern Hybridizations:

10–20 mg of complete RNA or 1–2 mg of poly(A)-RNA were fractionated by electrophoresis in a 1% agarose gel in the presence of 2.2 M formaldehyde. Transfer to a positively charged nylon membrane took place with the aid of a Vacuum Blotter with 10×SSC as transfer buffer for a period of two hours. Subsequently, the RNA was crosslinked covalently to the membrane by controlled-power UV irradiation. Hybridization of the specific probe (25 ng/ml) was carried out at 50° C. overnight in a buffer specially developed for the purpose of non-radioactive hybridization (DIG Easy Hyb, BOEHRINGER). The probe used in this case was amplified by means of the polymerase chain reaction from the 3' end of the coding sequence of the relevant h-sgk (nucleotide 980–1480) and simultaneously labeled by including DIG-dUTP in the reaction buffer. After the blots had been washed twice in 2×SSC at room temperature and in 0.5×SSC at 65° C., the labeled probe was detected by an ELISA using an anti-digoxigenin antibody coupled to alkaline phosphatase which produced a chemoluminescence reaction in CDP-Star (BOEHRINGER) which was detected by autoradiography (average exposure time about two minutes).

2. Western Blot Analysis:

Detailed of antibody production: The rabbits were immunized by using two peptides from the h-sgk amino acid sequence: Pos. 386-Pos. 404 (DPEFTEEPVPNSIGKSPDS), Pos. 416-Pos. 431 (EAFLGFSYAPPTDSFL). The two peptides (SEQ ID NOS 3 and 4, respectively) were conjugated to KLH and to MAP, respectively, as carrier and injected intracutaneously with complete and incomplete, respectively, Freund's edjuvant. The injection and blood-sampling protocol followed standard procedures. The immune sera were purified by affinity chromatography, and the antibody fractions were collected and used at a concentration of about 1 mg/ml.

Immunoblot analysis: About 60 mg of total cellular protein were fractionated by electrophoresis through an SDS/7.5% polyacrylamide gel and transferred to a nitrocellulose membrane. The membranes were blocked in 3% BSA/5% milk powder/0.06% Tween 20 in PBS overnight. Primary (affinity-purified anti-h-sgk) and secondary (horseradish peroxidase-conjugated goat anti-rabbit IgG, Bio-Rad) were each incubated in 3% BSA/0.06% Tween in PBS at room temperature for one hour. An enhanced chemoluminescence kit (ECL, Amersham) was used for immunodetection.

3. In Situ-hybridization:

15 mm frozen sections underwent counterfixation in 4% formaldehyde for 20 minutes, followed by two washing steps in 100 mM phosphate buffer pH 7.2 for 5 minutes each time. Proteinase K treatment (1 mg/100 ml) was followed by incubation in 0.1 M triethanolamine/0.225% acetic acid for 10 minutes. After renewed washing with 100 mM phosphate buffer, the sections were dehydrated in an ascending alcohol series. Prehybridization took place in hybridization buffer at 50° C., and the hybridization was carried out overnight. The probe used corresponds to the probe described for the Northern blots. Detection took place by enzymatic cleavage of an X-phosphate solution catalyzed by an alkaline phosphatase coupled to anti-digoxigenin antibodies.

What is claimed is:

1. An isolated nucleic acid coding for the human cell volume-regulated kinase (h-sgk) consisting of the amino acid sequence shown in SEQ ID NO:2.

2. An isolated nucleic acid consisting of the nucleotide sequence shown in SEQ ID NO:1.

3. A nucleic acid consisting of approximately the region of nucleotide position 980 to 1480 of the nucleic acid sequence as claimed in claim 2.

4. A nucleic acid encoding an amino acid sequence of the peptide encoded by the nucleic acid of claim 3.

5. An isolated nucleic acid whose sequence corresponds to an RNA, which is capable of hybridizing under conditions of Northern hybridization or in situ hybridization at 65° C., in the sense or antisense direction, to nucleotide sequences in the region corresponding to nucleotide position 980 to 1480 of SEQ ID NO:1.

6. A nucleic acid fragment coding for an immunogenic fragment of the human cell volume-regulated kinase (h-sgk) consisting of at least one of the following amino acid sequences:

DPEFTEEPVPNSIGKDPDS (SEQ ID. NO: 3)
EAFLGFSYAPPTDSFL (SEQ ID. NO: 4).

7. A composition comprising the nucleic acid as claimed in claim 1 and a phannaceutically acceptable carrier.

8. A composition comprising the nucleic acid as claimed in claim 2 and a phannaceutically acceptable carrier.

9. A composition comprising the nucleic acid as claimed in claim 4 and a pharmaceutically acceptable carrier.

10. A composition comprising the nucleic acid as claimed in claim 3 and a pharmaceutically acceptable carrier.

11. A composition comprising the nucleic acid as claimed in claim 5 and a pharmaceutically acceptable carrier.

12. A composition comprising the nucleic acid as claimed in claim 6 and a pharmaceutically acceptable carrier.

13. The nucleic acid according to claim 5, wherein the capability of hybridizing is confined to approximately said region.

14. A composition comprising the nucleic acid in claim 6 and a pharmaceutically acceptable carrier.

15. The nucleic acid of claim 5, wherein the capability of hybridizing is confined to the region corresponding to nucleotide position 980 to 1480 of SEQ ID NO:1.

* * * * *